US008999261B2

(12) United States Patent
Benedetto

(10) Patent No.: US 8,999,261 B2
(45) Date of Patent: Apr. 7, 2015

(54) DEVICE FOR HAND DISINFECTION

(75) Inventor: Mariachiara Benedetto, Milan (IT)

(73) Assignee: Industrie de Nora S.p.A., Milan (IT)

( * ) Notice: Subject to any disclaimer, the term of this patent is extended or adjusted under 35 U.S.C. 154(b) by 143 days.

(21) Appl. No.: 13/555,512

(22) Filed: Jul. 23, 2012

(65) Prior Publication Data
US 2012/0285825 A1 Nov. 15, 2012

Related U.S. Application Data

(63) Continuation of application No. PCT/EP2011/051078, filed on Jan. 26, 2011.

(30) Foreign Application Priority Data

Jan. 28, 2010 (IT) .............................. MI2010A0109

(51) Int. Cl.
*A61L 2/22* (2006.01)
*A61L 2/00* (2006.01)
*A61L 2/03* (2006.01)

(52) U.S. Cl.
CPC .............. *A61L 2/0088* (2013.01); *A61L 2/035* (2013.01); *A61L 2/22* (2013.01); *A61L 2202/11* (2013.01); *A61L 2202/14* (2013.01)

(58) Field of Classification Search
CPC ....... A61L 2/00; A61L 2/0005; A61L 2/0082; A61L 2/0088; A61L 2/16; A61L 2/18; A61L 2/24; A61L 2202/00; A61L 2202/10; A61L 2202/11; A61L 2202/14; A61L 2202/25; C02F 1/46; C02F 1/461; C02F 1/46104

USPC ............. 422/291, 292, 28–30, 294, 297, 300, 422/305, 306; 204/275.1
See application file for complete search history.

(56) References Cited

U.S. PATENT DOCUMENTS

| 6,431,189 | B1 | 8/2002 | Deibert |
| 2006/0171843 | A1 | 8/2006 | Spears |
| 2007/0134127 | A1* | 6/2007 | Smith et al. ..................... 422/37 |

FOREIGN PATENT DOCUMENTS

| EP | 0978290 A2 | 2/2000 |
| JP | 11192180 A | 7/1999 |
| JP | 2000051328 A | 2/2000 |
| JP | 2009178640 A | 8/2009 |
| KR | 20090123278 A | 12/2009 |
| KR | 20090123297 A | 12/2009 |
| WO | 2006096991 A1 | 9/2006 |
| WO | 2009046563 A2 | 4/2009 |

OTHER PUBLICATIONS

Machine translation of KR2009012397, provided by esp@cenet. Retrieved Feb. 6, 2014.*
Search Report dated Mar. 29, 2011 in connection with patent application PCT/EP2011/051078, p. 1-6.
Search Report dated Sep. 9, 2010 in connection with patent application IT MI20100109, p. 1-4.

* cited by examiner

*Primary Examiner* — Timothy Cleveland
(74) *Attorney, Agent, or Firm* — Lucas & Mercanti, LLP

(57) ABSTRACT

The invention relates to an apparatus for hand washing and disinfection by nebulization of an in-situ electrolyzed active solution. The dispensed solution contains active chlorine optionally added with ozone or peroxides.

8 Claims, 1 Drawing Sheet

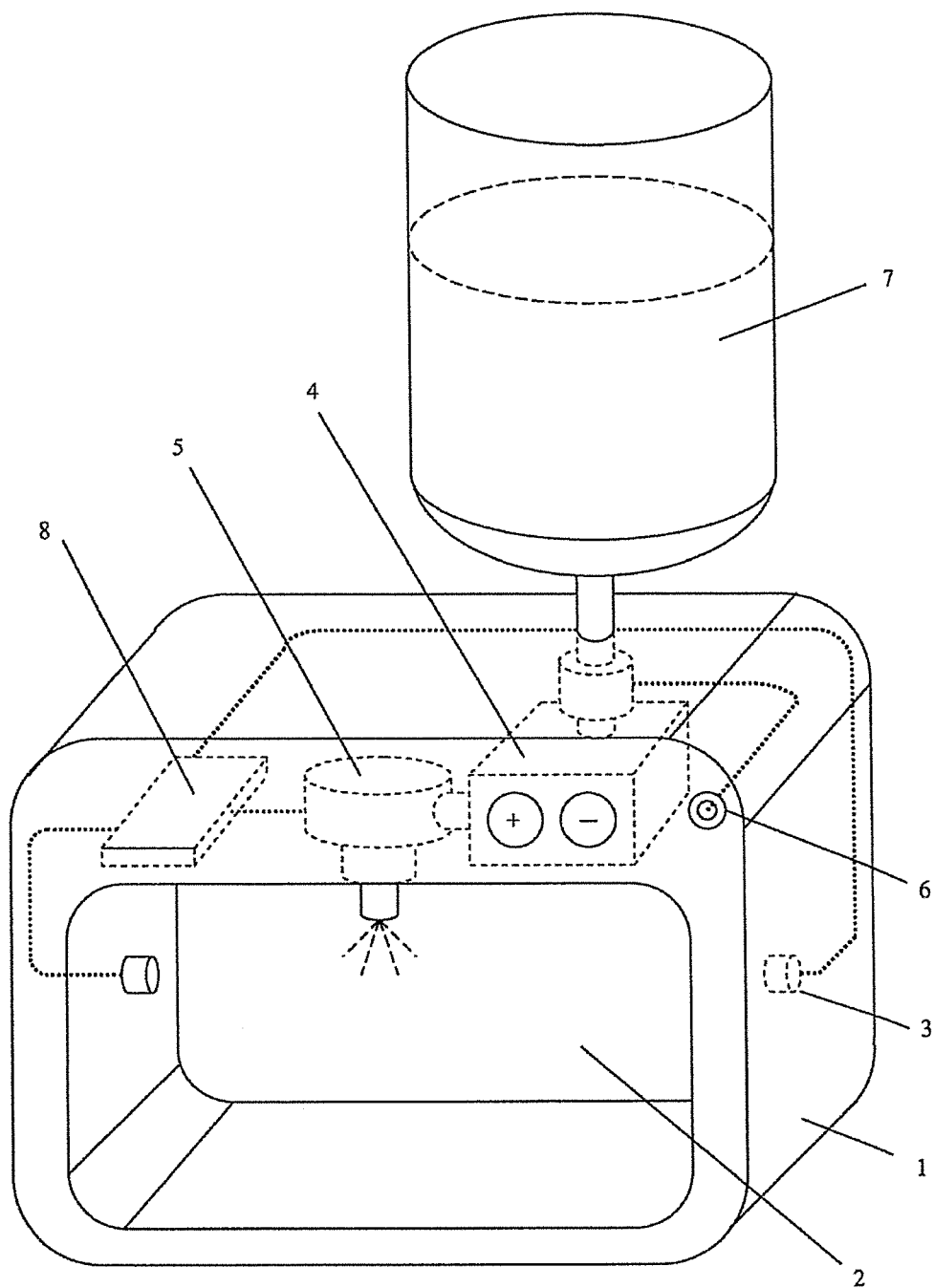

DEVICE FOR HAND DISINFECTION

CROSS-REFERENCE TO RELATED APPLICATION

This application is a continuation of PCT/EP2011/051078 filed Jan. 26, 2011, that claims the benefit of the priority date of Italian Patent Application No. MI2010A000109 filed Jan. 28, 2010, the contents of which are herein incorporated by reference in their entirety.

FIELD OF THE INVENTION

The invention relates to a system for producing and releasing a solution suitable for use in human hygiene, in particular to a point-of-use electrochemical system for production and release of a solution suitable for washing and disinfecting hands.

BACKGROUND OF THE INVENTION

Devices for the release of solutions or gels suitable for washing hands are present in several public places in addition to domestic environments. It is an increasingly common practice to fill common liquid soap dispensers with products containing disinfecting substances, for example having antiseptic properties, in order to get an improved protection in crowded or high-transit public places (airports and train stations, highway service stations, theatres, cinemas and venues for sports events). Alternatively, disinfecting solutions are provided in disposable soaked tissues, with the inconvenience of involving a waste product that needs to be subsequently dumped. Although useful, gels and solutions of common use do not offer a wide-spectrum protection. Broad spectrum antiseptic agents known in the art are, in fact, characterised by an excessive cost or by an insufficient or scarcely reproducible shelf-life. While in many cases the protection provided by a normal antibacterial product may be considered acceptable, there are other environments where a broader spectrum protection would be highly desirable, also for the sake of preserving public health. For example, this is the case with hospitals or clinics where expensive specific products are commonly used, but also with places where food is processed (e.g. kitchens of public restaurants, butcheries, bakeries and confectioneries) or distributed (e. g. canteens and restaurants).

The need for providing an efficient and economical system for hand disinfection in a wide range of environments has been hence identified.

SUMMARY OF THE INVENTION

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter. As provided herein, the invention comprises, under one aspect an apparatus for hand disinfection comprising a rigid body provided with a recess for hand insertion, an electrochemical cell provided with a timer, suitable for producing an oxidant solution by electrolysis of an aqueous electrolytic medium during a predefined time, a device for nebulising the oxidant solution inside the recess for hand insertion, at least one probe suitable for detecting hand insertion inside the recess, an actuator suitable for commanding the upload of a predefined volume of the aqueous electrolytic medium inside the electrochemical cell and the timed execution of the electrolysis, the probe and the nebulising device being connected to an electronic control board suitable for commanding the nebulisation of the oxidant solution based on the detection of the probe.

In a further aspect, the invention comprises an apparatus for hand disinfection comprising a rigid body provided with a recess for hand insertion, an electrochemical cell provided with a timer, the cell suitable for producing an oxidant solution by electrolysis of an aqueous electrolytic medium during a predefined time, a device for nebulising the oxidant solution inside the recess for hand insertion, and at least one probe suitable for detecting hand insertion inside the recess, the probe, the electrochemical cell and the nebulising device being connected to an electronic control board suitable for commanding the upload of a predefined volume of the aqueous electrolytic medium inside the electrochemical cell, the execution of the electrolysis and the nebulisation of the oxidant solution based on the detection of the probe.

To the accomplishment of the foregoing and related ends, the following description sets forth certain illustrative aspects and implementations. These are indicative of but a few of the various ways in which one or more aspects may be employed. Other aspects, advantages, and novel features of the disclosure will become apparent from the following detailed description.

BRIEF DESCRIPTION OF THE DRAWINGS

FIG. 1 illustrates a plan view of a device for hand disinfection according to an embodiment of the invention.

DESCRIPTION

Various aspects of the invention are set out in the accompanying claims.

In one embodiment, the invention comprises an apparatus suitable for producing and nebulising an oxidant solution having disinfecting properties, comprising a rigid body provided with a recess for the insertion of the hands. The invention further includes an electrochemical cell equipped with a timer suitable for producing an oxidant solution by electrolysis of an aqueous electrolytic medium during a predefined time and a device for nebulising the oxidant solution inside the recess for hand insertion, at least one probe suitable for detecting hand insertion inside the recess and an actuator suitable for commanding the upload of a predefined volume of the aqueous electrolytic medium inside the electrochemical cell and the timed execution of the electrolysis. The probe and the nebulising device are connected to an electronic control board commanding the nebulisation of the product oxidant solution based on the detection of the probe. The device of the invention may be used, for example, to produce in an efficient and cost-effective way, oxidant solutions containing species such as active chlorine, ozone or peroxides, characterised by a high antibacterial action at the time of production, but having a much too sharp decay time to allow their concentration being guaranteed even in the short term. For example, active chlorine may advantageously be used in the form of a hypochlorite and hypochlorous acid mixture at equilibrium, at a concentration of from about 20 to about 300 ppm. Below 20 ppm, the antibacterial action results in less efficiency, while at too high concentrations the aggressive action may be excessive to the human skin. A solution containing about 300 ppm of active chlorine would, nevertheless, have an insufficient stability to be stored and supplied as a product for dispenser refill, unless either stabilised with caustic soda at concentrations unsuitable for application on human skin, or provided in the form of organic species characterised by a slow release of chlorine, which are more toxic and remarkably more expensive. The in-situ point-of-use production of an oxidant solution containing active chlorine can have the advantage of being directly obtained at a concentration suitable for use with no stabilisation needed. Oxidant solutions containing active chlorine produced by electrolysis of alkali chloride brines, for example sodium chloride, may also contain a small amount of active oxygen, for example ozone or peroxide traces, which are then quickly decomposed. This can have the advantage of further increasing the efficiency of the antibacterial or biocide action of the product solution.

In one embodiment, the actuator of the apparatus allows uploading a predefined volume of an electrolytic aqueous medium—for example a brine of an alkali metal chloride such as sodium or potassium chloride—to the electrochemical cell and subjecting the same to electrolysis. In one embodiment, the predefined volume of electrolyte comprises between about 1 milliliter (ml) to about 20 ml. In one embodiment, the electrolysis of the electrolytic medium is carried out for a time of from about 1 second to about 5 seconds, until a suitable concentration of oxidant species, for example, from about 20 ppm to about 300 ppm of active chlorine with optional traces of ozone or peroxides, is attained. In one embodiment, the insertion of the hands in the recess after operating the actuator and the completion of the electrolysis are detected by a suitable probe, which in one embodiment comprises a photocell. When the insertion of the hands is detected, the electronic control board receives the signal of the probe and commands the actuation of the nebulisation device, for example, comprising an atomiser, through which the electrolytically-produced oxidant solution is sprayed on the hands.

In one embodiment, when the actuator is operated for a predefined number of times, for example 2 to 5 times, with no corresponding hand insertion in the appropriate recess being detected, the electronic control board nevertheless commands the nebulisation of the produced oxidant solution. This can have the advantage of avoiding that, upon repeatedly operating the actuator commanding the electrolysis of the electrolytic medium, an excessive accumulation of the oxidant solution takes place or the concentration thereof is increased to excessive values. For example, in a cell set up to produce an oxidant solution with an active chlorine concentration of 100 ppm with no possibility of uploading an additional volume of solution after the first electrolyte upload before the product discharge takes place, it is to be avoided that the actuator be operated in a rapid sequence for more than three consecutive times in order to prevent the concentration of active chlorine in the oxidant solution exceeding 300 ppm, which is considered the upper limit of the optimum interval.

In one embodiment, the invention comprises an apparatus suitable for producing and nebulising an oxidant solution having disinfecting properties, comprising a rigid body provided with a recess for the insertion of the hands, an electrochemical cell provided with a timer, suitable for producing an oxidant solution by electrolysis of an aqueous electrolytic medium during a predefined time, a device for nebulising the oxidant solution inside the recess for hand insertion, at least one probe suitable for detecting hand insertion inside the recess and an actuator suitable for commanding the upload of a predefined volume of the aqueous electrolytic medium inside the electrochemical cell, the timed execution of the electrolysis. The electrochemical cell, in addition to the probe and nebulisation device, is connected to an electronic control board which commands the upload of a predefined volume of electrolytic solution, the subsequent timed execution of electrolysis inside the electrolytic cell and the subsequent nebulisation of the product oxidant solution on the basis of the detection of the probe, optionally comprising a photocell. In this case, the apparatus may not include a further actuator as the function is carried out by the probe suitable for detecting the hand insertion. Also in this case, the predefined volume of electrolyte may be between about 1 ml and about 20 ml, and the electrolysis of the electrolytic medium may be carried out for a time of between about 1 second and about 5 seconds, until a suitable concentration of oxidant species is attained, for example, about 20 ppm to about 300 ppm of active chlorine, with optional traces of ozone or peroxides.

The composition of the product oxidant solution may be varied by acting on the composition of the aqueous electrolytic medium and on the nature of the electrodes, in particular of the anode, installed in the electrolytic cell, as will be evident to a person skilled in the art. For example, the generation of hypochlorite or hypochlorous acid may be obtained by using diluted sodium chloride brines, optionally acidulated to shift the equilibrium towards the hypochlorous acid species, and titanium anodes activated with catalysts based on oxides of transition metals such as ruthenium, iridium, palladium, titanium, zirconium or tantalum. Likewise, it is possible to produce solutions containing ozone (for example starting from tap water with anodes based on mixed oxides of tin and antimony or with deionised water with boron-doped diamond anodes), oxygen peroxide (for example from acid or alkaline electrolytes in cells provided with an air-fed gas-diffusion electrode) or active chlorine and mixed peroxidates such as percarbonate or persulphate (with tap water optionally added with sodium carbonate and boron-doped diamond anodes).

The concentration of the oxidant species in the product solution may be adjusted by acting on the active surface of the electrodes, on the current density, on the electrolysed volume and on the electrolysis duration. A person skilled in the art can easily determine the most favourable parameters for the preparation of the oxidant solution in a suitable composition range. The generation of oxidant solutions containing active chlorine, mainly in the form of hypochlorite, with optional traces of active oxygen, can have the advantage of providing a product with optimum disinfecting properties starting from an extremely cheap and handy electrolytic medium with reduced electrolysis times, also for small size electrolytic cells. For example, a load of 6 ml of a simple sodium chloride solution at 1-10 grams/liter (g/l) can generate 20-300 ppm of active chlorine in a time range of 1 to 2 seconds with a total anodic area of 6 to 21 $cm^2$ at a current density of 1 to 2 $kA/m^2$. The sodium chloride solution may be uploaded to the apparatus by means of a dispenser bottle like those commonly used for drinking water distribution, housed inside the rigid body or positioned externally thereto, for example, above the device, and put in fluid communication with the cell. In an alternative embodiment, the sodium chloride solution may be fed through disposable cartridges. In one embodiment, the sodium chloride brine may be prepared at the time of use, for example by dissolving a pre-dosed amount of sodium chloride, optionally as powder or tablet, in a predefined volume of water.

In one embodiment, the device is powered from grid, rechargeable batteries or solar panels, taken alone or in mutual combination.

In the embodiment shown in the FIG. 1, a device for hand disinfection comprises a rigid body 1 provided with a recess 2 for hand insertion of suitable dimensions. Inside rigid body 1, an actuator 6, for example a start button optionally connected to a central process unit, commands the upload of a predefined quantity of electrolyte, for example a salt solution contained in a dispenser bottle 7, to an electrochemical cell 4 and the subsequent timed execution of an electrolytic process inside the same cell 4 at a predefined current density. Inside recess 2 a suitable probe, for example a photocell 3, detects the hand insertion and sends a signal to an electronic control board 8, which in turn activates a device for nebulisation, for example, comprising an atomiser 5, in communication with the outlet of electrochemical cell 4 and fed with the product of the timed electrolysis comprising an oxidant solution-containing species with high antibacterial activity at a suitable concentration.

Some of the most significant results obtained by the inventors are described in the following example which is not intended to limit the extent of the invention.

EXAMPLE 1

An apparatus equivalent to the one illustrated in FIG. 1 was equipped with an undivided electrolytic cell provided with titanium anodes coated with a mixture of oxides of titanium, palladium, ruthenium and iridium, arranged face-to-face at a distance of 0.15 mm (millimieters) and characterised by a total surface of 21 $cm^2$. The cell was fed with a solution containing 4 g/l of sodium chloride contained in a dispenser bottle positioned above the rigid body and connected thereto by means of a calibrated loading device, commanded by a central process unit. The cell was also provided with an outlet for the gaseous by-products, interfaced to a relief valve engaged on the upper surface of the rigid body. The process central unit was set to alternately operate one of the two electrodes as anode and the other as cathode, reversing the polarity at every next operation of the start button provided as the actuator. The apparatus was run by setting a load volume of 6 ml of electrolyte, varying the duration and current density of the electrolytic process. An electrolysis time of 2 seconds at a 2000 $A/m^2$ current density proved sufficient to generate an oxidant solution containing 300 ppm of active chlorine, mostly as hypochlorite ion, together with peroxide traces. In this case, the electronic control board commanding the atomiser was set to discharge the product solution five seconds after pushing the start button, even in case the hand insertion in the apparatus were not detected by the photocell. By reducing the electrolysis time and current density set up in the central process unit, proportionally lower concentrations of active chlorine were obtained, whereupon the electronic board controlling the atomiser could be set to discharge the product oxidant solution after a higher number of idle cycles (for example, after the third consecutive operation of the actuator for concentrations of 100 ppm of active chlorine).

A person skilled in the art can easily make several changes to the described embodiments, without deviating from the scope of the invention; as said before, by acting on the electrolyte composition and the type of electrodes, different compositions of oxidant solution can be easily obtained as needed. It is also possible to substitute the undivided cell of the example, wherein each of the electrodes alternately works as anode and as cathode, with a cell provided with a separator (for example with a ceramic separator or with an ion-exchange membrane) and with non-interchangeable anode and cathode, optionally of distinct formulations. It is also possible to use either the central process unit controlling the electrolysis parameters, or a different central process unit, as the control electronic board of the nebulising means. It is also possible to provide that the control electronic board command the nebulisation of the solution after a predefined time even though the hand insertion is not detected, in order to discharge the unused oxidant solution.

The previous description is not intended to limit the invention, which may be used according to different embodiments without departing from the scopes thereof, and whose extent is univocally defined by the appended claims.

Throughout the description and claims of the present application, the term "comprise" and variations thereof such as "comprising" and "comprises" are not intended to exclude the presence of other elements or additives.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention before the priority date of each claim of this application.

What I claim is:

1. An apparatus for hand disinfection comprising a rigid body provided with:
   a recess for hand insertion;
   an electrochemical cell provided with a timer, configured to produce an oxidant solution by electrolysis of an aqueous electrolytic medium during a predefined time;
   a device for nebulizing the oxidant solution inside the recess for hand insertion;
   at least one probe suitable for detecting hand insertion inside the recess;
   an electronic control board configured to initiate upon activation the steps of:
      uploading a predefined volume of the aqueous electrolytic medium inside the electrochemical cell,
      subsequent timed execution of the electrolysis inside the electrochemical cell until a concentration of the oxidant solution containing from about 20 to about 300 ppm of active chlorine is maintained, and
      subsequent nebulization of the oxidant solution;
   wherein the activation of the electronic control board is based on the detection by the probe or consecutive triggering of an actuator a predetermined number of times, independently from the detection by the probe.

2. The apparatus according to claim 1, wherein the oxidant solution further contains traces of ozone or peroxides.

3. The apparatus according to claim 1, wherein the predefined volume is from about 1 to about 20 ml.

4. The apparatus according to claim 1, wherein the predefined time is from 1 to about 5 seconds.

5. The apparatus according to claim 1, wherein the probe suitable for detecting hand insertion comprises a photocell.

6. The apparatus according to claim 1, wherein the aqueous electrolytic medium is an alkali chloride brine supplied to the electrochemical cell from a dispenser bottle.

7. The apparatus according to claim 1, wherein the aqueous electrolytic medium is an alkali chloride brine supplied to the electrochemical cell from a disposable cartridge.

8. The apparatus according to claim 1, further comprising an electrical power supply from grid, rechargeable batteries or solar panels, alone or in mutual combination.

* * * * *